US009045439B2

(12) United States Patent
Sioli

(10) Patent No.: US 9,045,439 B2
(45) Date of Patent: Jun. 2, 2015

(54) PROCESS FOR THE PRODUCTION OF HIGH PURITY MELAMINE FROM UREA

(71) Applicant: Urea Casale SA, Lugano-Besso (CH)

(72) Inventor: Giancarlo Sioli, Cernobbio (IT)

(73) Assignee: Casale SA (CH)

( * ) Notice: Subject to any disclaimer, the term of this patent is extended or adjusted under 35 U.S.C. 154(b) by 0 days.

(21) Appl. No.: 13/626,539

(22) Filed: Sep. 25, 2012

(65) Prior Publication Data

US 2013/0028800 A1    Jan. 31, 2013

Related U.S. Application Data

(62) Division of application No. 12/920,730, filed as application No. PCT/EP2009/001294 on Feb. 24, 2009.

(30) Foreign Application Priority Data

Mar. 4, 2008  (EP) .................................... 08004013

(51) Int. Cl.
| | |
|---|---|
| C07D 251/60 | (2006.01) |
| C07D 251/62 | (2006.01) |
| C07D 251/52 | (2006.01) |
| C07D 251/46 | (2006.01) |
| B01J 19/06 | (2006.01) |
| B01J 19/18 | (2006.01) |
| B01J 19/00 | (2006.01) |

(52) U.S. Cl.
CPC ............ C07D 251/62 (2013.01); *C07D 251/52* (2013.01); *C07D 251/46* (2013.01); *B01J 19/006* (2013.01); *B01J 19/18* (2013.01); *B01J 19/1862* (2013.01); *B01J 19/1881* (2013.01); *B01J 2219/00083* (2013.01); *B01J 2219/00768* (2013.01); *C07D 251/60* (2013.01)

(58) Field of Classification Search
CPC .. C07D 251/60; C07D 251/62; C07D 251/52; C07D 251/46
USPC .................................................. 544/201, 203
See application file for complete search history.

(56) References Cited

U.S. PATENT DOCUMENTS

| | | | |
|---|---|---|---|
| 3,161,638 A | 12/1964 | Christoffel et al. | |
| 3,637,686 A | 1/1972 | Kokubo et al. | |
| 4,408,046 A | 10/1983 | Van Hardeveld | |
| 6,024,483 A | 2/2000 | Burke et al. | |
| 6,774,234 B1 | 8/2004 | Noe | |
| 6,790,956 B1 | 9/2004 | Coufal | |
| 6,870,050 B2 * | 3/2005 | Coufal et al. ................. | 544/201 |
| 7,176,309 B2 * | 2/2007 | Schroder et al. .............. | 544/203 |
| 7,375,223 B2 * | 5/2008 | Bairamijamal ................ | 544/201 |
| 7,414,130 B2 * | 8/2008 | Brunengo et al. ............. | 544/201 |
| 2004/0049034 A1 | 3/2004 | Coufal et al. | |
| 2004/0162429 A1 | 8/2004 | Noe et al. | |
| 2005/0131228 A1 * | 6/2005 | Schroder et al. .............. | 544/203 |
| 2007/0232801 A1 | 10/2007 | Bairamijamal | |
| 2007/0282102 A1 * | 12/2007 | Brunengo et al. ............. | 544/201 |

FOREIGN PATENT DOCUMENTS

| | | |
|---|---|---|
| WO | 95/06042 A1 | 3/1995 |
| WO | WO 2005080321 A1 * | 9/2005 |

OTHER PUBLICATIONS

Shiroshi, Akihiro et al., "Technical Development of Melamine Manufacture by Urea Process", Chemical Economy and Engineering Review, vol. 8, Feb. 1976, pp. 35-39, 47, 50.
Ullmann, "Ullmann's Encyclopedia of Industrial Chemistry", Ullmann, 2002, Sixth Ed., pp. 1 and 13.

* cited by examiner

Primary Examiner — Venkataraman Balasubramanian
(74) Attorney, Agent, or Firm — Akerman LLP

(57) ABSTRACT

The present invention concerns process for obtaining melamine at high purity characterized by comprising the steps of:—quenching a melamine melt, deprived of off-gases of the melamine synthesis and containing melamine impurities such as ammeline, ammelide and polycondensates, with an aqueous solution comprising ammonia under conditions such to substantially convert polycondensates into melamine, obtaining a melamine solution substantially free of polycondensates, recovering melamine from said melamine solution by melamine crystallization, obtaining melamine crystals and a melamine crystallization mother liquor,—treating said crystallization melamine mother liquor under conditions such to convert at least a portion of its ammeline content into ammelide and melammine, obtaining a treated mother liquid having at least a reduced ammeline content. The invention also concerns a high-pressure non-catalytic plant for the production of high-purity melamine implementing the above process and apparatuses suitable to be used in this plant.

11 Claims, 5 Drawing Sheets

PROCESS FOR THE PRODUCTION OF HIGH PURITY MELAMINE FROM UREA

CROSS-REFERENCE TO RELATED APPLICATIONS

This application is a divisional of U.S. patent application Ser. No. 12/920,730, filed Sep. 2, 2010, which is a national phase of PCT/EP2009/001294, filed Feb. 24, 2009, which claims priority to European Patent Application No. 08004013.2, filed Mar. 4, 2008. The entire contents of these applications is incorporated herein by reference.

FIELD OF APPLICATION

In its general aspect, the present invention relates to a high-pressure non catalytic process for the production of high purity melamine from urea.

In particular, the present invention relates to a process for purifying melamine from impurities like ureido-melamine, oxotriazines, melam, melem by an appropriate physical-chemical treatment.

The present invention also relates to high-pressure non-catalytic plant for the production of high-purity melamine.

PRIOR ART

The modern processes of melamine synthesis can be classified into two categories: the catalytic low-pressure processes and the non-catalytic high-pressure processes. All processes are characterised by three process stages: a) melamine synthesis by urea pyrolysis; b) melamine purification and recovery; c) off-gas treatment. An overview of the prior art is given in Ullmann's Encyclopedia of Industrial Chemistry, Vol. A 16, p. 171-181 (1990).

In a high-pressure non-catalytic process, a urea melt from the off-gas scrubber is fed to the high-pressure reactor, operated at a pressure in the range of 70 bar to 200 bar and at a temperature in the range of 360-420° C. The urea is pyrolised to melamine according to the following equation:

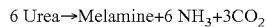

6 Urea→Melamine+6 $NH_3$+3$CO_2$

The product of the reaction is a raw melamine, in liquid phase, so-called melamine melt, containing impurities of various types, which are commonly precursors or derivatives of the melamine molecule itself, or un-reacted urea. Depending on the production process, raw melamine has a concentration of impurities in the range from 6 to 12% by weight. They include at least oxy-amino-triazines (i.e. ammeline, ammelide), melamine poly-condensates (i.e. melam, melem, melon), ureido-melamine, urea, dissolved ammonia and carbon dioxide.

Nevertheless melamine users require a commercial product of very high purity, usually not less than 99.8%. Therefore raw melamine has to be purified by separating said impurities, until reaching the required purity level.

This problem has generated much work in this technical field, aiming to find out adequate solutions for obtaining high purity melamine in a simple way and at reasonable investment and operating costs.

In this regard, according to the technology mainly used in high-pressure non-catalytic melamine production processes, the purification/recovery of pure melamine takes place via the dissolution of the melamine melt, as obtained by the high-pressure reactor, and the subsequent crystallisation of melamine from the aqueous solution.

A basic purification process of the above type is disclosed in U.S. Pat. No. 3,161,638 (Allied Chemical corporation). This document discloses a process for producing high-purity melamine in which all effluents from the melamine synthesis reactor (liquid and gaseous phases) are de-pressurized and cooled to approximately 160° C. in the presence of a water solution (recycled aqueous mother liquor hereinafter described) so as all the melamine, the non-reacted urea and the various impurities, pass into solution to be processed downstream.

The quenched effluent (solution) is first passed into a low-pressure stripper to remove a gaseous phase, consisting substantially of water-saturated ammonia and carbon dioxide, by direct contact with steam, the gaseous phase being recycled to the urea synthesis plant, and then to a digester in which said solution is heated to approximately 170° C. in the presence of anhydrous ammonia added to the warm solution until it reaches the level of 12-15% by weight. During the stay in the digester under these conditions, the polycondensates are almost totally transformed into melamine and, to a lesser extent, into oxy-amino-triazines (OAT).

The purified ammoniacal solution from the digester is filtered and then fed to a crystallizer where the temperature is lowered to 40-50° C., thus allowing the crystallization of the larger part of the melamine. The presence of ammonia in the crystallizer serves to maintain OAT in solution and thus to separate a product characterized by a high degree of purity (+99.9% by weight). The crystallized melamine is then separated in a liquid/solid separator from an aqueous stream containing the OAT formed in reaction and in the various equipments of the aqueous circuit due to the hydrolysis of melamine.

This aqueous stream (called mother liquor) which, other than OAT, still contains residual melamine (about 0.8-1% by weight) and large amount of ammonia, cannot be recycled directly to the quench apparatus, because, otherwise, OAT content would continue to increase and, once the saturation concentration is reached, it would precipitate in the crystallizer contaminating the product.

Therefore, the process according to U.S. Pat. No. 3,161,368 provides for the purification of the mother liquor before recycling it to the quench by first separating ammonia in a ammonia recovery section and then by cooling the resulting ammonia-free solution so as to cause precipitation and separation of OAT which is then eliminated from the aqueous cycle.

However, the process illustrated above, although it is currently used industrially in several plants, requires a high energy consumption and costly equipments in particular for separating OAT from the mother liquor.

An improvement of the process illustrated above is disclosed in US 2004/0162429 (Eurotecnica). In particular, this patent application discloses a process for the production of high purity melamine in which the liquid phase output from the pyrolysis reactor containing melamine, non-reacted urea, OAT and polycondensates is fed to a downstream reactor (Post reactor)—that operates in equal temperature and pressure conditions to those of the pyrolysis reactor—where it comes into intimate contact with superheated anhydrous gaseous ammonia added in amounts equal to from 1:10 to 1:1 by weight on the raw liquid melamine.

The superheated ammonia passing through the liquid mass of the raw melamine permits the transformation of OAT into melamine, so reducing its content to a value lower than 6,000 ppm, while polycondensates content is reduced to less than 1% by weight.

The purified liquid melamine is then treated in a quenching apparatus at 160-170° C. in the presence of 10% by weight minimum of ammonia aqueous solution to remove the polycondensates. The resulting aqueous solution in output from the quenching apparatus and containing 7-8% by weight of melamine is cooled causing a high purity melamine to separate by crystallization from a mother liquor.

In this way, it would be possible to recycle a major portion of the mother liquid (about 80%) directly to the quenching apparatus without contaminating the product crystals.

However, the process illustrated in US 2004/0162429 still requires a costly post-reactor which affects in a significant way the investment and operating costs of the high-pressure melamine plants. Moreover, the relatively low concentration of melamine has the consequence of handling large volumes of mother liquor.

SUMMARY OF THE INVENTION

The technical problem underlying the present invention is therefore that of providing a process for obtaining melamine at high purity in a simple and reliable manner as well as with low energy consumption and investment costs, so as to overcome the above-mentioned drawbacks of the prior art.

This problem is solved by a process for obtaining melamine at high purity characterized in that it comprises the steps of:

quenching a melamine melt, deprived of off-gases of the melamine synthesis and containing melamine impurities such as ammeline, ammelide and polycondensates, with an aqueous solution comprising ammonia under conditions such to substantially convert polycondensates into melamine, obtaining a melamine solution substantially free of polycondensates, recovering melamine from said melamine solution by melamine crystallisation, obtaining melamine crystals and a melamine crystallization mother liquor, treating said crystallization melamine mother liquor under conditions such to convert at least a portion of its ammeline content into ammelide and melammine, obtaining a treated mother liquid having at least a reduced ammeline content.

In the process of the invention, the quenching step is preferably carried out at a temperature in the range of 150° C. to 190° C. with an aqueous solution comprising ammonia at a concentration in the range from 20% to 35% for a time from 10 minutes to 30 minutes to obtain a melamine in which the melamine concentration is in the range from 8 to 16% by weight.

Most preferably, said melamine melt is quenched at a temperature of 160° to 180° C. and at a pressure of 15-80 bar as determined by the total vapour pressure of the solution at the selected temperature and ammonia concentration.

Most preferably, the melamine concentration in the solution is comprised in the range from 9% to 13% by weight.

According to an embodiment of the invention, gaseous ammonia is also added to said aqueous solution comprising ammonia in the quenching step.

It has been found that under the selected operating conditions of the quench of melamine melt according to the present invention, impurities associated to the melamine, namely polycondensates as formed during melamine synthesis, are totally converted into melamine by reaction with ammonia. At the same time, the selected operating conditions are such to avoid an additional formation of OAT.

According to the present invention, the melamine and ammonia solution, containing OAT substantially in form of ammeline and ammelide, obtained in the quenching step is passed to a crystallization step, where it is cooled down to 30-60° C., preferably 40-50° C., causing the separation of melamine crystals of very high purity. The crystallization pressure results to be slightly above the atmospheric one, as determined by the vapour pressure of the ammoniated solution at the selected temperature. In the selected conditions ammeline $C_3N_3(NH_2)_2(OH)$ and ammelide $C_3N_3(NH_2)(OH)_2$ remain into solution.

According to the present invention, it has been found that, after separation of melamine crystals, the resulting mother liquor may be treated in a way to obtain the conversion of the larger part of the present ammeline into melamine, and of a minor part of it into ammelide. This has the double advantage of recovering some more melamine, and of transforming ammeline, poorly soluble in aqueous ammonia, into the much more soluble ammelide, allowing the recycle of the mother liquor to the quench step without the risk of precipitating ammeline in the next crystallization step.

According to the invention, such advantageous treatment of the mother liquor comprises the step of heating up the mother liquor at a temperature in the range of 150 to 190° C. for a period of time ranging from 1 to 4 hours before recycling it for the purpose of quenching and diluting the melamine melt delivered as reactor product.

Gaseous ammonia may also be added in the mother liquor treatment step to compensate for ammonia losses at the crystallization step or during ammelide removal as explained below.

This treatment step, which is made on the total flow of the mother liquor, before its recycle to the quenching and dilution step, differs substantially from the treatment provided by the U.S. Pat. No. 3,161,638, in which all ammonia is stripped off the solution, with great expense of energy, making both ammeline and ammelide to precipitate in solid form, to be filtered out, due to their poor solubility into the de-ammoniated water.

In addition, it has been found that the above-described heating step not only allows the ammeline conversion to melamine and ammelide but is also able to hydrolyse, in form of $NH_3$ and $CO_2$, urea non converted in the main reaction of melamine synthesis, coming with the melamine melt, and passing downstream the quenching step.

According to another aspect of the present invention, to avoid a build-up of ammelide in the closed loop of the mother liquor up to its solubility limit, risking the precipitation of ammelide during the melamine crystallization, the process further comprising the steps of:

separating a portion of mother liquor from the flow of mother liquor obtained after said heating step, substantially removing ammelide from said portion of mother liquor, and returning said portion of mother liquor substantially deprived of ammelide to said flow of mother liquid.

According to the invention, the portion of mother liquor separated from the flow of mother liquor obtained after said heating step is very small and is preferably comprised in the range of 5% to 20% by weigh.

Preferably, the removal of ammelide is carried out by de-ammoniating (stripping ammonia from) said separated portion of the mother liquor causing ammelide to precipitate and by separating the solid ammelide by filtration. After removal of the solid by filtration, the filtrate is returned back as such to the main mother liquor loop.

Further features and advantages of the present invention will appear more clearly from the following non limiting description of some embodiments of the method for obtaining melamine at high purity according to the invention, made with reference to the attached drawings.

DETAILED DESCRIPTION OF PREFERRED EMBODIMENTS

Figure 1:
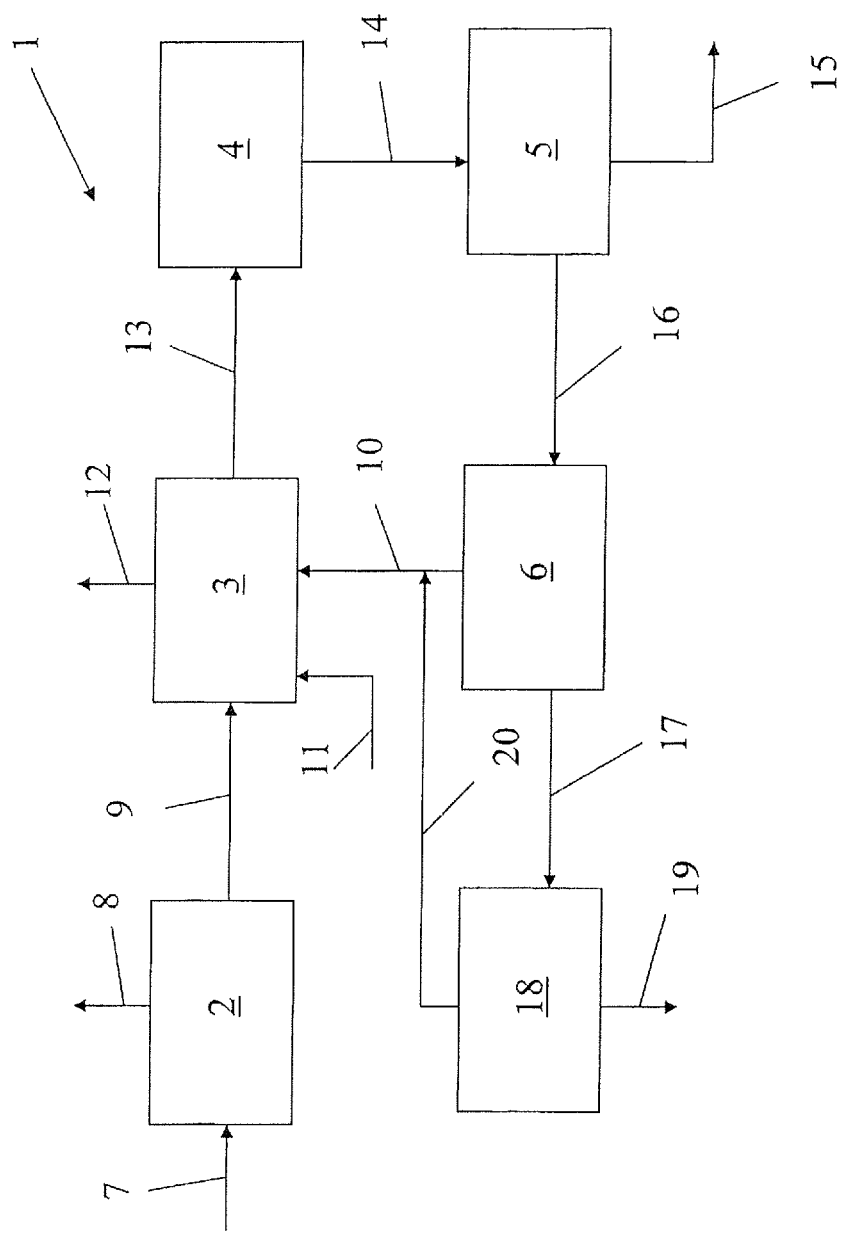
FIG. 1 shows a flow diagram of a melamine plant according to the present invention.

With reference to FIG. 1, a flow diagram of a plant-system for the manufacture of melamine from urea in a high-pressure process is shown.

In this melamine plant, which is indicated in its entirely with reference number 1, block 2 indicates a high-pressure reactor for melamine synthesis, block 3 indicates a quenching section for a melamine melt obtained in the reactor 2, block 4 indicates a melamine crystallisation section, block 5 indicates a liquid/solid separator for recovering melamine crystals of high purity and block 6 indicates a mother liquor treatment section for ammeline conversion.

Generally, in the present description and in the enclosed claims, and where it is not differently indicated, by the terms: "feeding or connecting means or flow line", it is intended to mean pipelines, connecting lines or ducts, pumps, compressor, ejectors or other devices of known type, which are used for transporting a liquid or gaseous flow from a location to another one in the plant.

Flow line 7 indicates a flow of liquid urea fed to the reactor 2 in which it is converted into melamine by pyrolysis. The reactor 2 usually operates at a pressure in the range of 70 bar to 200 bar and at a temperature in the range of 360-420° C.

The reacted mass is discharged by the reactor as two separate outputs, namely a gas flow 8 comprising ammonia and carbon dioxide and melamine vapours, and a flow 9 of raw melamine in liquid phase or melt which also contains some impurities such as OAT and polycondensates.

The gaseous flow 8 is normally recycled to the urea synthesis plant after separation of the melamine vapours (which are in turn returned to the reactor 2) in a conventional gas scrubbing unit (not shown).

On the contrary, the flow 9 of raw melamine is fed to the quenching section 3 where it is brought into intimate contact with a flow 10 of mother liquor, the latter coming from the treatment section 6 for ammeline conversion, in the manner that will be better disclosed in the following description, obtaining a melamine solution in concentrated ammonia-water where the polycondensates present are substantially fully converted into melamine.

The quenching section 3 is kept at a temperature of 150-190° C., under autogenously pressure, and is crossed by a small flow of gaseous ammonia, injected through line 11, while the excess is relieved through line 12.

The melamine solution discharged from the quenching section 3 is fed, through the flow line 13, to the crystallisation section 4 where the temperature is lowered to 30° C.-60° C., under autogenously pressure, causing the precipitation of crystals of very high-purity melamine, while the residual impurities and residual melamine remain into the solution.

The liquid stream containing the residual impurities and residual melamine (so-called mother liquor), and the crystallized melamine are discharged from the crystallisation section 4 and fed, through the flow line 14, to the liquid/solid separation section 5 where crystallized melamine is separated from the mother liquor.

Melamine crystals, as discharged by the flow line 15, are wet of mother liquor, which is removed by the usual technique of washing the crystals cake with water, obtaining a filtrate (containing dissolved melamine), which is returned to the mother liquor loop. Crystals are dried and delivered to the final packing.

From the separation section 5 the mother liquor is transferred, through the flow line 16, to the treatment section 6, where the liquid flow is heated up to 150-190° C., under autogenously pressure, and is kept in that condition for a time of 1 to 4 hours, depending on the operating temperature (the higher the temperature, the shorter the residence time). In this way, the ammeline in solution converts mainly into melamine, and to a lesser extent into ammelide.

Finally, the treated mother liquor is closing the loop by recycling, through the flow line 10, to the quenching section 3.

A very minor part of the mother liquor from section 6 is purged off through the flow line 17, to avoid an excessive build up of ammelide inside the mother liquor loop, and therefore risking the precipitation of ammelide during melamine crystallization. This stream is de-ammoniated and possibly neutralised in a ammelide removal section 18 obtaining the precipitation of ammelide, which is separated by filtration and discharged through the flow line 19, while the filtrate, containing melamine, is returned to the mother liquor loop through the flow line 20.

Figure 2:
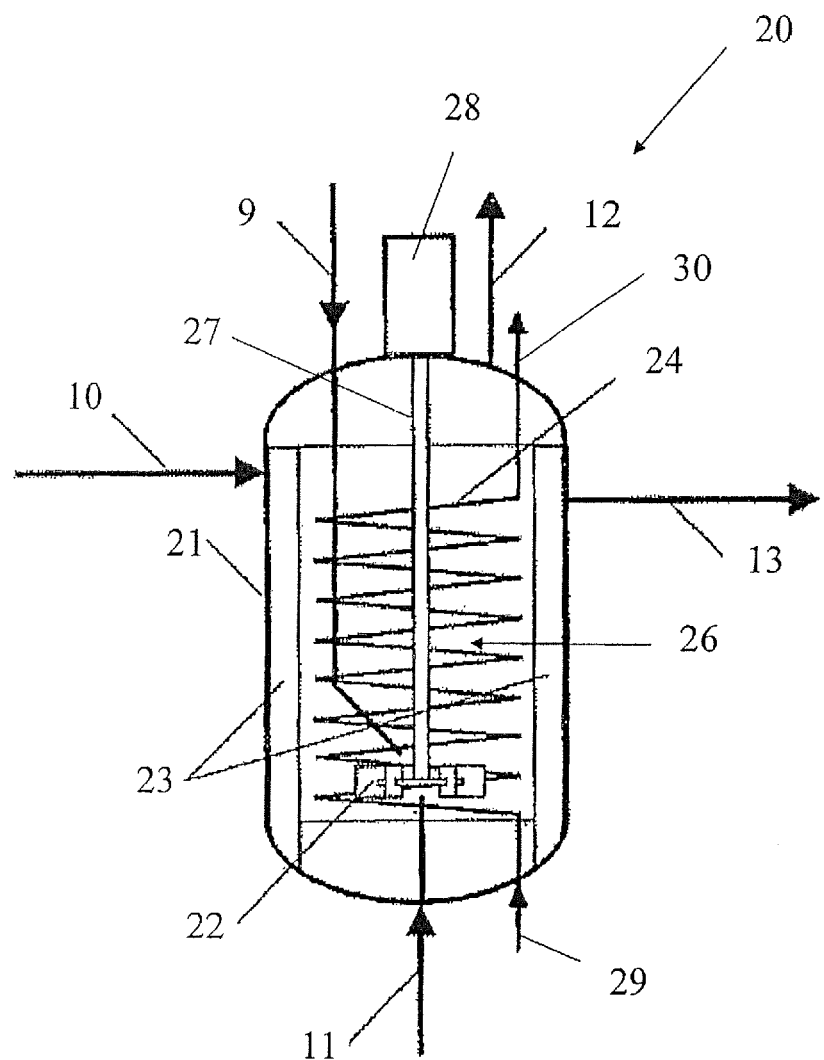
FIG. 2 shows a quench apparatus of the melamine plant of FIG. 1 according to an embodiment of the present invention.

FIG. 2 shows an apparatus according to an embodiment of the present invention for melamine quenching suitable to be used in the quenching section 3 of the melamine plant of FIG. 1. This quenching apparatus is indicated, in its entirety, with reference number 20.

The apparatus 20 comprises a vessel 21, of cylindrical, vertical type, which is designed and constructed so as to be effectively operated at a pressure substantially equal or below the operating pressure of the reactor 2, for example a pressure of 20-100 bar, preferably 30-70 bar and at an operating temperature of the melamine quenching preferably in the range of 150-190° C.

The vessel 21 is internally provided with a mechanical agitator indicated in its entirety with 26 and baffles 23 extending vertically from the shell of the vessel 21 for transferring to the liquid under agitation a significant deal of power. The agitator 26 includes a vertical shaft 27 extended along the vertical axis of the vessel 1 from its top to the lower portion of the vessel 21, and an impeller 22 at the lower end of the shaft 27. The agitator impeller 22 may be of turbine, or of propeller type and preferably it is a flat-blades turbine. The agitator 26 is controlled by a suitable motor 28 situated external to the vessel 21.

The vessel 21 is also internally provided with heat transfer coils 24 which may be realised as pipes internally crossed by a heat transfer fluid, as for instance by a stream of diathermic oil or pressurised boiling water. In particular, the heat transfer fluid enters the vessel 21 and the coils through a inlet pipe 29 and is discharged from them through a outlet pipe 30.

The vessel 21 also comprises suitable openings (not shown) for the inlet of the mother liquor coming from the treatment section 6, for the inlet of melamine melt coming from the reactor 2, for the inlet and the outlet of gaseous ammonia and for the outlet of melamine solution.

In particular, according to the present invention, the mother liquor is introduced in the vessel 21 through the pipe 10. Melamine melt is admitted through pipe 9, which preferably extends inside the vessel 21 from its top to the proximity of a upper part of the agitator impeller 22. In this way, advantageously, as soon as the melt arrives to the upper part of the agitator impeller 22, it is immediately dispersed inside the liquid phase present in the vessel 21.

Gaseous ammonia is fed to the vessel by pipe 11, which is advantageously extended inside the vessel 21 from its bottom to a lower part of the agitator impeller 22. In this way, as soon as ammonia arrives to the lower part of the agitator impeller 22, it is immediately subdivided into very fine droplets, and dispersed inside the liquid phase present in the vessel 21. Surplus ammonia is relieved through pipe 12

According to the invention, in the vessel 21, melamine melt is contacted with mother liquor and quenched at a temperature from 150° C. to 190° C., preferably 160° C.-180° C., while the resulting solution is kept into intimate contact with gaseous ammonia, for a time in the range from 15 minutes to 90 minutes.

In this way, melamine passes into solution at a concentration preferably from 8% to 16% by weight while, at the same time, some of the impurities such as polycondensates, as formed in the reactor 2, are converted to melamine by reaction with ammonia, obtaining the practical disappearing of polycondensate content in the resulting melamine solution.

In this regard, according to the invention, ammonia present in the mother liquor and gaseous ammonia are preferably introduced into the vessel 21 so as to keep a concentration in said solution in the range from 20% to 35% by weight, in the stated range of temperatures, at the equilibrium pressure reached by the quench vessel. In addition, gaseous ammonia is advantageously highly dispersed and distributed in the liquid mass thanks to the agitator impeller 22 which realizes a high efficient gas-liquid contacting system.

In the vessel 21, the temperature conditions are controlled by the heat exchanging fluid flowing in the coils 24 which removes heat from the vessel 21 to keep the total liquid mass at the desired temperature.

The liquid phase discharged out from the vessel 21 is transferred to the successive crystallisation section 4 of the plant 1, where it is immediately cooled down to the final crystallisation temperature, in the range of 30 to 60° C. under autogenously pressure. The transfer may be simply done under the pressure differential through pipe 13 by means of a level control device or by a pump.

Figure 3:
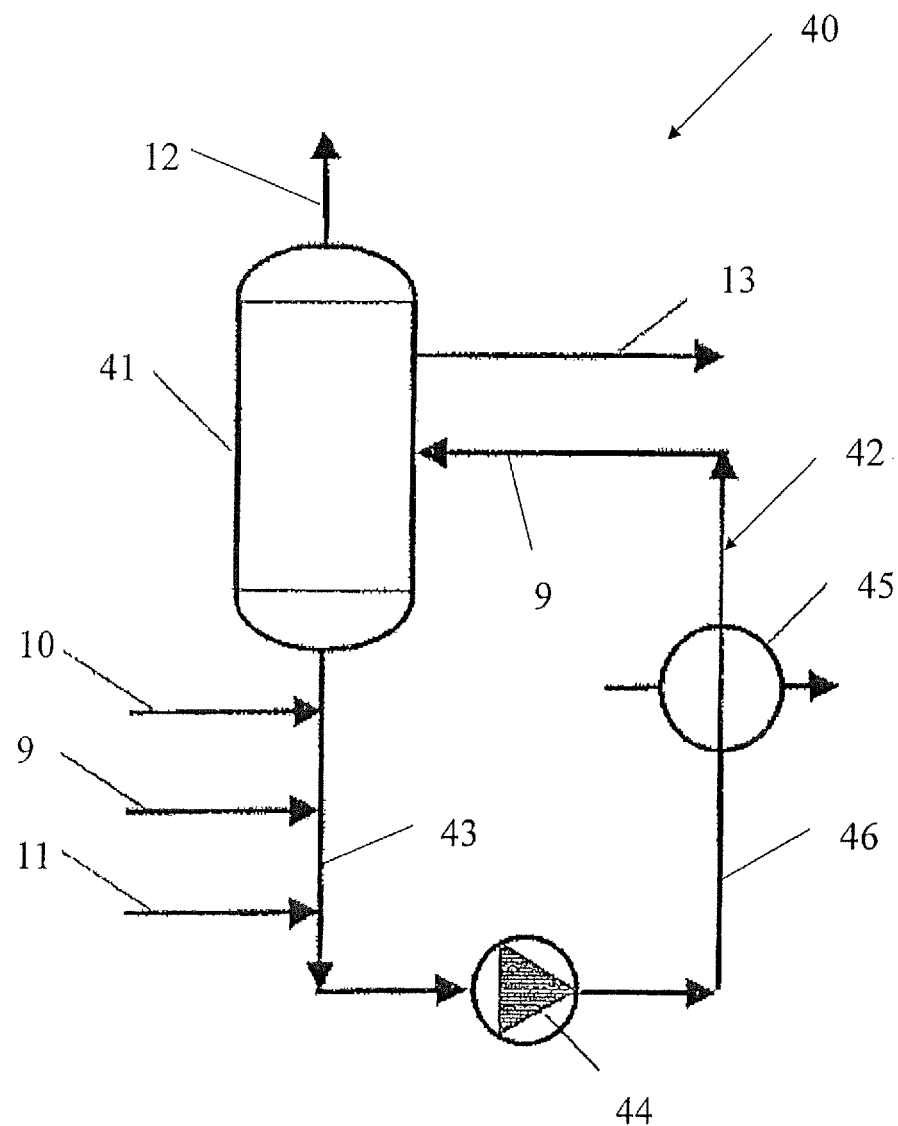
FIG. 3 shows a quench apparatus of the melamine plant of FIG. 1 according to another embodiment of the present invention.

FIG. 3 shows an apparatus according to another embodiment of the present invention for melamine quenching suitable to be used in the quenching section 3 of the melamine plant of FIG. 1. This quenching apparatus is indicated in its entirety with reference number 40.

To the elements of the apparatus 40 of FIG. 3 which are structurally or functionally equivalent to corresponding elements of the apparatus 20 of FIG. 2 the same reference numbers of the latter elements are assigned.

The apparatus 40 includes a vessel 41 and closed loop, indicated in its entirety with reference number 42, external to the vessel 41. The closed loop 42 includes a suction pump 44, a heat exchanger 45, a pipe 43 connecting the bottom of the vessel 41 to the pump 44, a pipe 46 connecting the pump 44 to the heat exchanger 45 and a pipe 47 connecting the heat exchanger 45 to the vessel 41.

In this embodiment, all fluids to be intimately mixed together, namely mother liquor coming from the flow line (pipe) 10, melamine melt coming from the flow line (pipe) 9 and gaseous ammonia coming from the flow line (pipe) 11 are mixed in the pipe 43 and the resulting liquid/gaseous phase is allowed to circulate continuously in the closed loop 42 and in the vessel 41 through the pump 44. This allows ammonia to be finely distributed in the liquid mass.

The control of the liquid temperature is performed by the heat exchanger 45 crossed at the process side by the liquid/gaseous phase from which heat is removed as necessary by a heat exchanging fluid.

A flow of melamine solution is continuously discharged out from the vessel 41 through pipe 13 and sent to the crystallisation step in the section 4 as indicated above.

Figure 4:
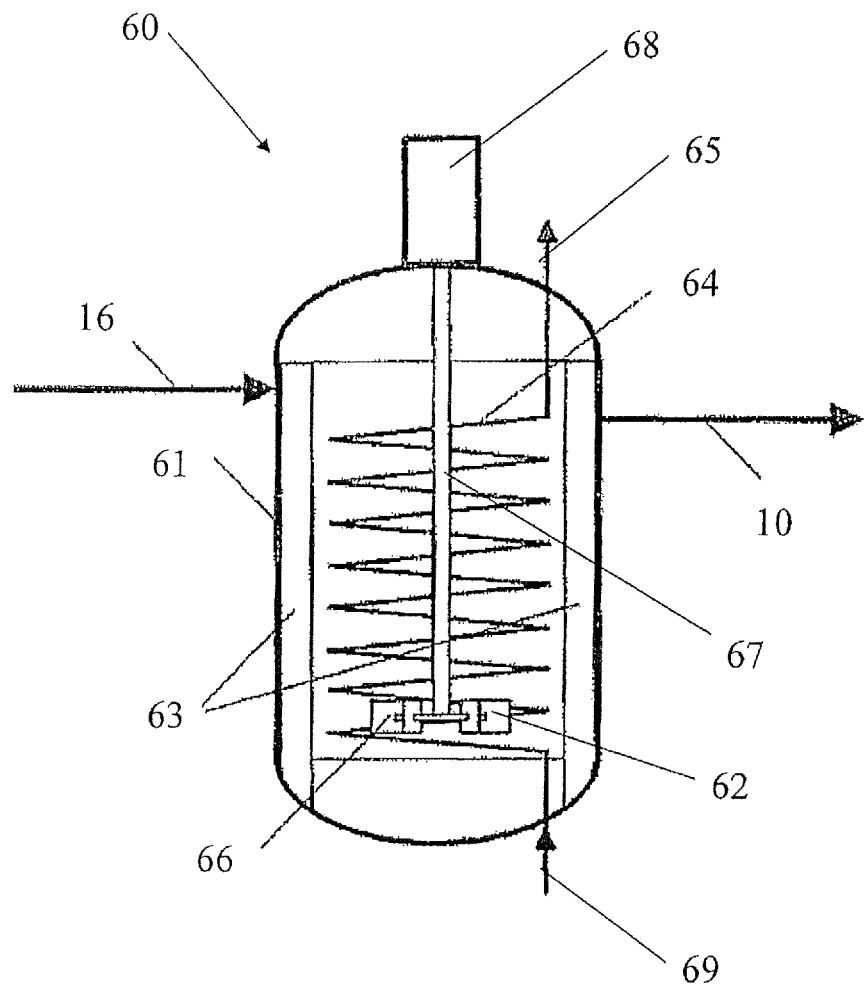
FIG. 4 shows an apparatus according to an embodiment of the present invention for treating crystallization melamine mother liquor in order to convert ammeline into ammelide and melammine.

FIG. 4 shows an apparatus according to an embodiment of the present invention for treating crystallization melamine mother liquor in order to convert ammeline into ammelide and melammine. This apparatus is indicated, in its entirety, with reference number 60 and is suitable to be used in the treatment section 6 of the melamine plant of FIG. 1.

The apparatus 60 comprises single pressure vessel 61 of total volume sufficient to allow the mother liquid flow the desired residence time at the selected temperature. The pressure vessel 61 is internally provided with a mechanical agitator 66 and baffles 63 extending vertically, helping the liquid under agitation to have heat transferred from the coil 64, internally crossed by a heating fluid, as for instance condensing steam. In particular, the heat transfer fluid enters the vessel 61 and the coils 64 through a inlet pipe 69 and is discharged from them through a outlet pipe 65.

The agitator 66 includes a vertical shaft 67 extended along the vertical axis of the vessel 61 from its top to the lower portion of the vessel 61, and an impeller 62 at the lower end of the shaft 67. The agitator impeller 62 may be of turbine, or of propeller type and preferably it is a flat-blades turbine. The agitator 66 is controlled by a suitable motor 68 situated external to the vessel 61.

The vessel 61 is also internally provided with heat transfer coils 24 which may be realised as pipes internally crossed by a heat transfer fluid, as for instance by a stream of diathermic oil or steam. In particular, the heat transfer fluid enters the vessel 21 and the coils 24 through a inlet pipe 29 and is discharged from them through a outlet pipe 30.

The mother liquor is introduced in the vessel 61 through the pipe 16, while the treated liquid exits through the pipe 10.

Figure 5:
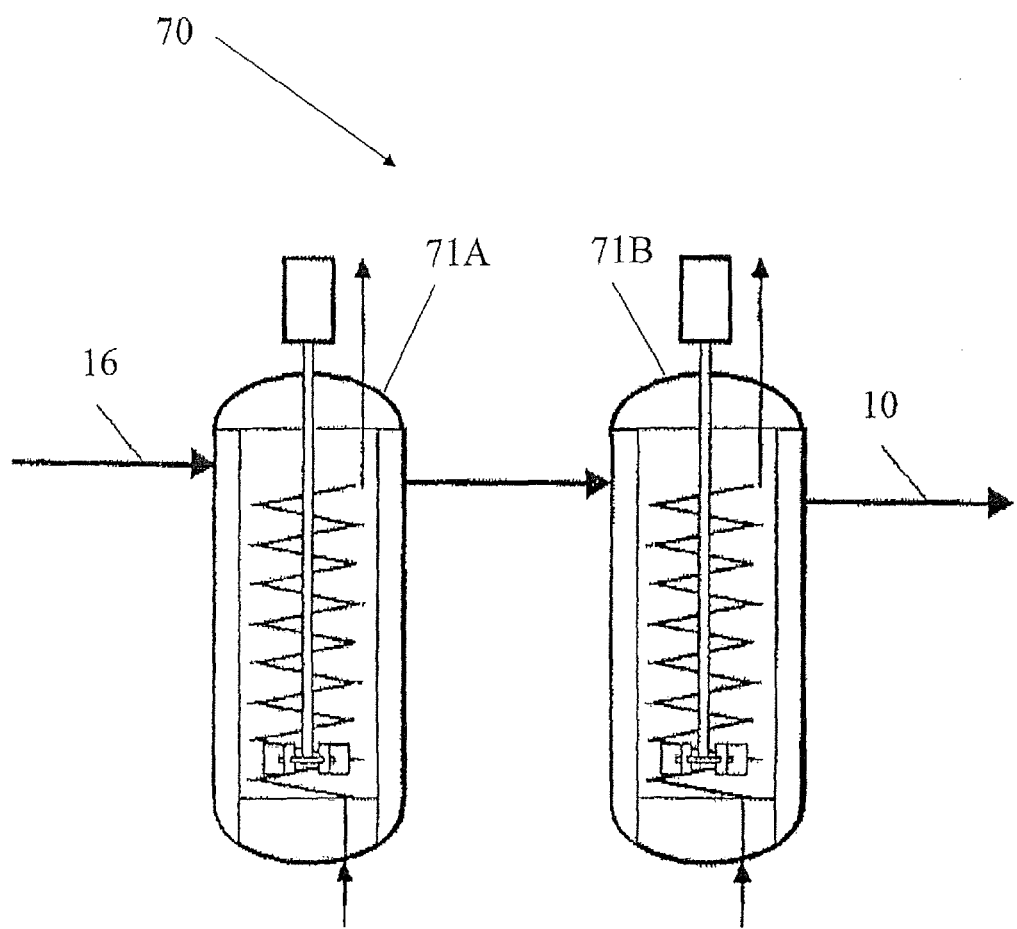
FIG. 5 shows an apparatus according to another embodiment of the present invention for treating crystallization melamine mother liquor in order to convert ammeline into ammelide and melammine.

FIG. 5 shows an apparatus according to another embodiment of the present invention for treating crystallization melamine mother liquor in order to convert ammeline into ammelide and melammine. This apparatus is indicated, in its entirety, with reference number 70 and is suitable to be used in the treatment section 6 of the melamine plant of FIG. 1.

The apparatus 70 comprises two pressure vessels 71A and 71B, of the same configuration as for vessel 61 described above, set in series on the liquid flow. This configuration has the advantage of using much smaller vessels, i.e having a volume lower than in case of single vessel 61.

According to another embodiment of the invention (not shown), the mother liquor coming from the solid/liquid separation section 5 may be pre-heated at the desired temperature in an appropriate exchanger upstream the vessel 61 of apparatus 60 or the vessel 71A of apparatus 70. In this case, the heat transfer coils 64 in vessel 61 or vessels 71A and 71B are not required anymore.

In the vessel 61 of apparatus 60 and in the vessels 71A and 71B of apparatus 70, due to the temperature increase, the ammonia solution constituting the mother liquor rises in pressure up to 15-80 bar pressure, depending on the ammonia concentration used.

The treated mother liquor, depleted in ammeline, and enriched in melamine (and some ammelide) is transferred to the quenching section 3, which operates at approximately the same temperature and pressure of the ammeline conversion section 6.

The following examples are intended to better show as the invention may be practiced, and the advantages thereof, but they are not to be interpreted as limiting its scope.

EXAMPLE 1

A sample of 100 g of melamine melt, as delivered by a high-pressure technology after separation of the off gas, and kept in liquid phase at 390° C., 80 bar pressure, had the following composition (percentages by weight):
melamine 89.7%
OAT 1.0%
poly-condensates 2.2
unconverted urea 5.0%
dissolved $NH_3$ 1.3%
dissolved $CO_2$ 0.8%

The sample has been quickly transferred into a stirred tank reactor, kept at 170° C., where 800 g of aqueous solution of ammonia at 31% strength had been previously placed. The vessel reached an internal pressure of 41 bar.

After 10 minutes under stirring, the reactor content was quickly transferred in a further, agitated vessel, equipped for cooling down rapidly to about 40° C. the obtained melamine solution. After reaching the desired temperature, the vessel internal pressure was about 1 bar.

A sample of liquid phase, submitted to analysis, showed a melamine concentration of 0.67%, ammeline 0.08%, which is less than its solubility limit in ammonia 31% strength, ammelide 0.02%, very far from its solubility limit (2%). Poly-condensates were not detectable. Urea resulted to be partially hydrolysed. Separated melamine crystals were of very high purity.

EXAMPLE 2

A mother liquor of the following composition (percentages by weight):
Melamine 0.84%
ammeline 0.12%
ammelide 0.1%
ammonia 30.4%
water balance to 100%
similar to the one recovered in Example 1 from the melamine crystallization step, has been fed in continuous, at the rate of 800 g/h, into a 1-liter stirred tank reactor heated to maintain the temperature constant to 180° C. Gaseous ammonia has been injected in the same reactor to raise the pressure up to 66 bar. By keeping constant the internal liquid level, the product was discharged, cooled and analysed. Ammeline was substantially disappeared, and converted by approx 80% into melamine, the balance into ammelide.

The same experiment has been repeated in milder conditions, by halving the ammonia concentration and operating at 170° C., bar pressure. In order to observe a substantial conversion of ammeline the flow rate had to be reduced down to 250 g/h. Meanwhile the main product of the reaction was ammelide.

EXAMPLE 3

The process according to the invention for obtaining melamine at high purity was carried out in a pilot plant according to FIG. 1.

A melamine melt having the same composition described in Example 1 was delivered by the high-pressure urea reactor 2.

This melamine melt was fed, at a rate of 100 kg/h, to the quenching section 3 in a stirred tank-type reactor (vessel 21) equipped as described above with reference to FIG. 2, the reactor 21 accommodating 150 liters of liquid volume and the quenching and dilution process taking place in the reactor 21 at 170° C.

The same reactor 21 received in continuous 810 kg/h of recycled, aqueous ammonia solution containing 250 kg/h of ammonia, and about 550 kg/h of water, the balance being mainly dissolved melamine and ammelide (recycled mother liquor). Said aqueous ammonia solution came from the ammeline conversion section 6, operating also at 170° C. and the quenching reactor 21 and the ammeline conversion section 6 operated at approximately the same, autogenously internal pressure of 44 bar.

The temperature of the quenching reactor 21, receiving the melamine melt at 380-390° C. and the ammonia solution at 170° C., was temperature-controlled at 170° C. by adequate cooling.

The liquid overflowing in continuous from the quenching reactor was a 10.7-10.9% strength solution of melamine, practically free of melamine poly-condensates. It was de-pressurized and fed in continuous to the crystallization section 4 in a cooler-crystallizer of about 1 $m^3$ volume, wherein the temperature of the process matter was kept at 45° C. The pressure of the crystallizer stabilized at 1.2 bar.

Melamine crystals precipitated, forming with the mother liquor a slurry, which was gradually extracted from the crystallizer, and fed to a centrifuge, which provided the crystals separation, and washed with demineralised water, while the filtrate mother liquor was collected in a tank, at atmospheric pressure.

The mother liquor, which was saturated by 0.84% melamine, and contained 0.12% ammeline and 0.17% ammelide, was fed in continuous, at a rate of about 940 liters/h, to the ammeline conversion section 6 in a stirred tank reactor (vessel 60), provided by an internal steam coil, heating the liquid and keeping it at 170° C. as described above with reference to FIG. 4. A small flow of gaseous ammonia was also introduced, to compensate for the losses at the crystals separation in the reactor 60, up to reach an internal pressure of 44 bar. The reactor volume was 2 $m^3$, providing then a liquid phase residence time of about 2 hours.

Thanks to this operation, the poorly soluble ammeline was converted into melamine and ammelide, allowing to re-circulating the aqueous ammonia solution (mother liquor) without the risk of ammeline precipitation during the melamine crystallization step. In addition, some urea (0.45%) left in solution as residual from the melamine melt, was effectively hydrolysed in this reactor 60.

The 80% of the treated mother liquid stream was re-sent directly to the quench section 3 while the remaining 20% of the treated mother liquid stream was purged off to remove ammelide, in the average about 0.4 kg/h, to avoid its excessive build-up in the process loop. The removal was done in ammelide removal section 18 by stripping away the dissolved ammonia, which makes ammelide insoluble in the residual water and separating ammelide by filtration. Then, the mother liquid stream substantially deprived of ammelide and still containing some melamine, was recovered from the treatment section 18 and returned to the process loop in the mother liquid stream to be recycled to the quench section 3.

In this way, the concentration of OAT in the process loop never reached the solubility limit, above which it could precipitate and contaminate the produced melamine. In addition, the process yield was very high, namely more than 98% of melamine having high purity (more than 99.8%) was recovered from the original melt containing melamine as such, or under form of poly-condensates and OAT.

EXAMPLE 4

A study was been carried out with the aim of reducing as much as possible the fraction of mother liquor to be purged off for the elimination of ammelide, after its generation from ammeline, as shown in the preceding examples, avoiding at the same time the risk of ammeline or ammelide precitation in the aqueous ammonia solution at the melamine crystallization step in the crystallization section 4.

According to this study, it was found that operating the plant of the preceding Example 3 in the same conditions, but by reducing the purging from 20% to 10% of the re-circulating aqueous ammonia solution (recycled mother liquid), the risk of OAT precipitation at melamine crystallization is avoided by 5% increase of the ratio between aqueous ammonia solution and melamine melt at the quenching section 3.

Furthermore, purge reduction to 5% of the recycled mother mother was possible by increasing of 20% the aqueous ammonia solution/melamine melt ratio at the quenching section 3.

The invention claimed is:

1. A high-pressure non-catalytic plant for the production of high-purity melamine comprising:
    a reactor for melamine synthesis;
    a quenching section for obtaining a melamine solution from a melamine melt discharged from the reactor;
    a melamine crystallization section for the melamine solution discharged from the quenching section and a liquid/solid separation section for separating crystals from a melamine mother liquor, wherein said reactor and said sections are in fluid communication to each other;
    a treatment section comprising heat transfer means for thermally treating a melamine crystallization mother liquor for ammeline conversion;
    means for feeding a flow of melamine crystallization mother liquor exiting said liquid/solid separation section to said treatment section; and
    means for feeding a flow of treated mother liquor exiting said treatment section to said quenching section.

2. The high-pressure non-catalytic plant according to claim 1, further comprising:
    an ammelide removal section,
    means for feeding a portion of the flow of the mother liquor exiting said treatment section to the ammelide removal section, and
    means for recycling the mother liquor exiting the ammelide removal section to said quenching section.

3. The high-pressure non-catalytic plant according to claim 1, wherein said quenching section comprises an apparatus for quenching said melamine melt comprising a vessel provided with at least an opening for the inlet of melamine mother liquid, melamine melt and gaseous ammonia as separated flows or mixed flow and with at least an opening for the outlet of said melamine solution, means for intimately distributing ammonia in said melamine solution and means for controlling the temperature of said melamine solution.

4. The high-pressure non-catalytic plant according to claim 3, wherein said means for intimately distributing ammonia in said melamine solution are provided inside said vessel and comprises an agitator having a vertical shaft and an impeller at the lower end of the shaft.

5. The high-pressure non-catalytic plant according to claim 4, wherein said impeller is a flat-blades turbine.

6. The high-pressure non-catalytic plant according to claim 3, wherein said ammonia and said melamine melt are fed in said vessel to the proximity of said impeller.

7. The high-pressure non-catalytic plant according to claim 3, wherein said means for controlling the temperature of said melamine solution are provided inside said vessel and comprises heat transfer coils internally crossed by a heat exchange fluid.

8. The high-pressure non-catalytic plant according to claim 3, wherein said means for intimately distributing ammonia in said melamine solution comprises a suction pump provided outside said vessel in fluid communication with it, said suction pump being fed said mother liquid, said melamine melt and said gaseous ammonia as a mixed flow.

9. The high-pressure non-catalytic plant according to claim 3, wherein said means for controlling the temperature of said melamine solution comprises a heat exchanger provided outside said vessel in fluid communication with it, said heat exchanger being crossed by a heat exchange fluid and, on the process side with said melamine melt and said gaseous ammonia as a mixed flow.

10. The high-pressure non-catalytic plant according to claim 1, wherein said treatment section comprises an apparatus for treating said melamine crystallization mother liquor comprising at least a vessel provided with an opening for the inlet of melamine crystallization mother liquid and an opening for the outlet of treated mother liquid, means for stirring said melamine crystallization mother liquor and means for heating said melamine crystallization mother liquor.

11. The high-pressure non-catalytic plant according to claim 10, wherein it comprises two vessels set in series in fluid communication to each other.

* * * * *